United States Patent
Powell et al.

(10) Patent No.: US 9,791,388 B2
(45) Date of Patent: Oct. 17, 2017

(54) CONVEYOR SYSTEM

(71) Applicant: Kromek Limited, Sedgefield (GB)

(72) Inventors: Andrew Keith Powell, Sedgefield (GB); John Atkins, Sedgefield (GB)

(73) Assignee: Kromek Limited, Sedgefield (GB)

( * ) Notice: Subject to any disclaimer, the term of this patent is extended or adjusted under 35 U.S.C. 154(b) by 0 days.

(21) Appl. No.: 15/307,720

(22) PCT Filed: May 1, 2015

(86) PCT No.: PCT/GB2015/051276
§ 371 (c)(1),
(2) Date: Oct. 28, 2016

(87) PCT Pub. No.: WO2015/166262
PCT Pub. Date: Nov. 5, 2015

(65) Prior Publication Data
US 2017/0059494 A1    Mar. 2, 2017

(30) Foreign Application Priority Data
May 2, 2014   (GB) .................................. 1407811.7

(51) Int. Cl.
*B65G 17/12*    (2006.01)
*G01N 23/10*    (2006.01)
*B65G 17/46*    (2006.01)

(52) U.S. Cl.
CPC ............. *G01N 23/10* (2013.01); *B65G 17/46* (2013.01); *B65G 2201/0244* (2013.01);
(Continued)

(58) Field of Classification Search
CPC .... B65G 17/002; B65G 17/12; B65G 17/123; B65G 2201/0244; G01N 23/04; G01N 9/24; G01N 23/10; G01N 23/083
(Continued)

(56) References Cited

U.S. PATENT DOCUMENTS 3,244,458 A  *  4/1966 Frost .................... B62D 55/065
                                                        198/690.2
3,961,701 A  *  6/1976 Paddock ................ B65G 17/32
                                                        198/803.11
(Continued)

FOREIGN PATENT DOCUMENTS

DE          10220435 C1      10/2003
EP          2696196 A1       2/2014
(Continued)

OTHER PUBLICATIONS

Savage, John, "International Search Report" for PCT/GB2015/051276, dated Jul. 24, 2015, 4 pages.

*Primary Examiner* — James R Bidwell
(74) *Attorney, Agent, or Firm* — Winstead PC (57) ABSTRACT

A conveyor system for use with a scanning apparatus for scanning of contained materials such as liquids within containers such as bottles. The system includes a transverse conveyor having a conveyor surface, a plurality of container support modules each adapted to seat on the conveyor surface. Each container support module includes a lower surface that sits upon the conveyor surface of the conveyor and upper part in which a container-receiving recessed portion is defined.

41 Claims, 1 Drawing Sheet

(52) U.S. Cl.
   CPC .. *B65G 2201/0261* (2013.01); *B65G 2203/04* (2013.01); *G01N 2223/639* (2013.01)

(58) Field of Classification Search
   USPC .......................... 198/867.11, 803.14, 867.08
   See application file for complete search history.

(56) References Cited

U.S. PATENT DOCUMENTS

| | | | | |
|---|---|---|---|---|
| 5,101,966 A | * | 4/1992 | Lapeyre | B65G 17/08 |
| | | | | 198/803.14 |
| 5,429,226 A | * | 7/1995 | Ensch | B65G 17/44 |
| | | | | 198/803.14 |
| 8,245,839 B2 | * | 8/2012 | Tajima | B28B 13/04 |
| | | | | 198/803.14 |

FOREIGN PATENT DOCUMENTS

| | | |
|---|---|---|
| GB | 2435458 A | 8/2007 |
| WO | WO-2009024818 A1 | 2/2009 |
| WO | WO-2010/028474 A1 | 3/2010 |
| WO | WO-2010/091493 A1 | 8/2010 |
| WO | WO-2010/136790 A1 | 12/2010 |
| WO | WO-2013/178431 A1 | 12/2013 |
| WO | WO-2014/107675 A2 | 7/2014 |

\* cited by examiner

CONVEYOR SYSTEM

This invention relates to a conveyor system for use with a scanning apparatus for the scanning of contained materials such as liquids and the like, especially within containers such as bottles and to a method of conveying contained materials such as liquids and the like, especially within containers such as bottles, to and through such a scanner. In a more complete embodiment the invention relates to a scanning apparatus and method for the scanning of contained materials such as liquids and the like.

The invention in particular relates to objects comprising containers of contained materials which by their nature will be expected to have a single generally homogeneous composition, for example fluid compositions such as liquids, including mixtures, solutions, emulsions, suspensions etc, like flowable compositions such as gels, pastes, creams, fine powders, and the like, aerosols etc. Where reference is made herein by example to contained liquids in liquid containers such as bottles it should be appreciated that the invention is equally applicable to all such liquid, partly-liquid and other flowable materials having this essential mixed and generally homogeneous character when contained.

The scanning apparatus and method is in particular a radiological scanner for the determination of information relating to the composition of the contained material. The invention particularly relates to an apparatus and method making use of high energy radiation such as x-rays or gamma-rays to scan objects where it is desirable to gain information about the internal contents and/or composition of the contained material.

The principle of scanning objects with high energy radiation such as x-rays or gamma-rays, particularly to generate image information in the form of a transmission radiograph, is widely employed for example in the security industry, but might also be employed in other areas, for example, without limitation, medical imaging, imaging for quality control purposes or the purposes of determining the integrity of the structure, or the like.

The invention is particularly useful in relation to use in a security or like situation for the detection of contraband liquid materials, for example explosives or other dangerous or prohibited materials. A particularly significant example of such used is in the screening of containers of unknown contents in an airport/airline or other enhanced security context or a customs control. The invention is discussed below by way of example in such a context. However the invention is not limited to security applications but can be applied in all circumstances where it might be desirable to gain information about the internal contents and/or composition of a contained liquid or liquid sample, for example for identification purposes, for stock control or quality control purposes, to monitor changes and especially degradation over time, and other applications.

It is desirable to scan the contents of objects such as, for example bottles, at security and customs checkpoints to gain information about content based on radiation received at a detector after interaction with the object and obtain an indication that the contents of the object do not constitute a threat to security or a breach of customs regulations. It is also desirable to scan the contents of objects for other purposes such as quality control, content verification, degradation monitoring etc.

To ensure that the contents of an object are what they are claimed to be, it may be useful to scan the object and contents so that a high energy and for example ionising radiation beam traverses a cross section of the object. Systems which convey objects through a scanner for example on a belt conveyor to generate an image are widely used for such purposes and existing protocols are in place for such systems.

However it can be possible to obtain an indication of the materials composition from a numerical analysis of the resultant transmitted radiation beam intensity data, for example by comparing the results of that analysis with a reference dataset relating to materials of known composition and/or to known contraband or other target materials.

The transmission of x-rays through a material can be given by the exponential attenuation law, as follows:

$$I/I_o = \exp[-(\mu/\rho)\rho t] \quad (1)$$

where
- $\mu/\rho$ = Mass attenuation coefficient (a material property which is characteristic of the weighted elemental composition of a material and the energy at which it is scanned);
- $I$ = final intensity;
- $I_o$ = Initial intensity;
- $\rho$ = density of the material; and
- $t$ = thickness of the material.

Thus by looking at the variation in the x-ray transmission as a function of changes in the thickness "t" of a material, for example, deductions can be made about the mass attenuation coefficient and the density of the material. These two parameters are characteristic of different materials and so materials identification becomes possible.

Instrumentation has been developed which is intended to non-invasively identify target liquids and like materials (that is, materials having similarly generally homogenous composition throughout) held within sealed containers. The target liquids or like materials may be liquids or like materials which pose a security threat if carried on-board an aircraft, liquids containing dissolved narcotics, or liquids requiring quality control, for example. According to techniques disclosed in International Patent Application No. PCT/GB2008/050711 (Publication No. WO2009/024818), a container may be irradiated with a beam of x-rays and the transmission response of the container and its liquid or like contents measured using an energy selective detector such as cadmium telluride or germanium.

When the object being scanned is a contained material which by its nature will be expected to have a single generally homogeneous composition, for example being a fluid composition such as a liquid as above described in a container, the analysis problem is potentially simplified when compared with scanning of inhomogeneous objects or packaging containing multiple objects by the expected homogeneity of the contained material and the container itself. Even so both the contained material and the container itself are subject to individual component variables, such as: the type of contained material, the composition or concentration of a contained material, the path length of high energy ionising radiation in the contained material, the material from which the container is made, and the thickness of the wall of the container, for example.

To enable these to be resolved when the radiation data collected from transmission through the container and its liquid or like contents is processed, and in particular to minimize complications attributable to fill level of partly filled bottles, irregular bottle shape and the like, known systems embodying the principles above described have been developed in which a bottle is scanned by being held in a fixed position and a scan performed through bottle and contents in a controlled manner using for example a simple pencil beam.

The fixed relationship and the simple beam geometry reduce unnecessary variable complexity in the transmission data and simplify its processing to resolve compositionally useful information about the contents. However the individual and discrete nature of the scanning operation reduces throughput as each bottle or other container must be placed in turn in the scanner.

Conventional security scanners are known which use x-rays and the like to scan objects as they pass through a scanning zone on a conveyor such as a moving belt conveyor. Such apparatus are standard in airport and other security and customs control situations. However the loss of control of orientation means they are unsuitable for contained materials such as liquids in bottles as the above problems arise.

It is desirable to develop a scanning protocol that confers a faster throughput rate. It is particularly desirable to develop a scanning protocol that is readily adaptable to existing systems with reduced additional footprint and/or cost.

In accordance with the invention in a first aspect, a conveyor system for use with a scanning apparatus for the scanning of contained materials such as liquids and the like, especially within containers such as bottles, comprises:

a transverse conveyor having a conveyor surface;

a plurality of container support modules each adapted to seat on the conveyor surface;

wherein each container support module comprises a lower surface that sits upon the conveyor surface of the conveyor and an upper part in which a container receiving recessed portion is defined.

The invention is applied to the support for passing through a scanner of contained materials such as liquids and the like, especially within containers such as bottles. Where further discussion herein considers liquids in bottles it will be appreciate that this is by way of exemplification. Many of the principles of the invention can be expected to apply to all contained materials comprising liquid, partly-liquid and other flowable materials having an essential mixed and generally homogeneous character when contained.

In use, a bottle or like container is placed on the support module and received in the recess in the support module, the support module is seated on the conveyor surface, and the bottle or other container is therefore stably held in a fixed position and orientation relative to the conveyor surface. In use the conveyor then acts to convey the bottle and support module to and through a suitable scanning apparatus in familiar manner.

The invention confers advantages over prior art security scanning systems in which bottles are held stationary and scanned one by one in that it is compatible with established continuous moving conveyor systems and scanning protocols and offers higher throughput rates.

It overcomes a particular problem in simply using established moving conveyor systems or scanning protocols, for example by placing a bottle on the belt directly or in a tray such as it often provided for scanning of loose objects. A particular problem in modifying moving conveyor systems for the conveyance of bottles and like containers, particularly those with a conventional circular cross-section and a tendency to roll, is the necessity of retaining the bottle in a stable and fixed relationship relative to the belt, so that its position is known as it passes through the scanning zone, so that its orientation is known, and so that the contents are not disturbed.

The invention achieves this by providing a recess in the upper surface of the support module, such that in use with the support module seated on the conveyor surface, the bottle or other container is therefore stably held in a fixed position and orientation relative to the conveyor surface.

A support module conformed in this manner provides a simple, versatile and effective solution to the problem of conveying bottles or other like containers to and through a scanning zone defined in a scanner. It overcomes the disadvantages associated with the static batch process scanning in the referenced prior art. Instead it allows for a system of scanning bottles or like containers, and their liquid or similar contents, in a continuous through the scanner protocol which more closely parallels existing preferred protocols and security scanning applications, whether in bespoke parallel apparatus or via suitable modification to existing scanner systems.

The support module requires sufficient rigidity to hold the container in such a stable and fixed position and orientation relative to the conveyor surface once the container is in place, but it may still be desirable to provide a degree of resilience, especially with regard to the recess in the upper surface of the support module. In a possible embodiment therefore, at least the portion of the support module comprising the recess in the upper surface is resiliently deformable and for example comprises flexibly resilient material. For example the recess in the upper surface is configured in use to be resiliently deformable as a bottle is placed therein, into a deformed configuration where the container is held stably and rigidly in a fixed position and orientation. This might allow a single recessed unit to accommodate a range of bottle or other container shapes/sizes, and/or to provide a degree of cushioning of the contents.

The support module may include a collar portion adapted in use to encircle the neck of a bottle to retain the bottle more stably and rigidly in a fixed position and orientation.

The support module comprises a lower surface that sits upon the conveyor surface. The lower surface is preferably adapted to tend to retain the support module in a stable seated position on the conveyor surface as the conveyor is caused to move. For example the lower surface comprises or has a surface covering of a high friction material. Additionally or alternatively, the support module may comprise one or more engagement members to engage a lower surface of the support module in a seated position on the conveyor surface.

Desirably, the support module should have a known x-ray attenuation profile, and more desirably yet a negligible x-ray attenuation profile. This allows any x-ray attenuation attributable to the support module to be easily subtracted from a signal produced during a scan in use, or to be ignored, as the case may be. A support module with a very low x-ray attenuation provides for more widespread applicability for a range of applications, in particular for example where it is desirable to scan a range of containers with a range of potential responses, and the complication of removing attenuation attributable to the container might make the data harder to interpret.

Desirably, the support module may be fabricated from a light weight/low density material.

Materials meeting some or all of these requirements might include open and closed cell cellular materials such as cellular polymeric materials, for example including polymerised styrene, vinyl and imide foams.

In a particular preferred case that offers many of the above advantages, the support module may comprise a gas-filled envelope so configured as to define a container-receiving recessed portion. In use, the gas-filled envelope comprising the container support module has container-receiving recessed portion defined in an upper surface, at least when a container is received therein.

The support module comprises a gas-filled envelope comprising at least one closed cellular volume defined by a suitable gas-impermeable web material which is particular a flexible thin film material inflated to the desired extent with a gas. The module is for example inflated to the desired extent and/or otherwise configured to tend to deform when a bottle or other container is placed in position, and thereby to tend to define a suitable recess in use. For example, the gas-filled envelope may be partly inflated to the extent that such a deformation is effected in use. Additionally or alternatively, as described below, the gas-filled envelope may be given a cellular structure or otherwise be specifically structured to define a suitable receiving recess in an upper surface of the support module.

The gas filled envelope therefore serves as a resiliently-deformable cushion-like structure. This might allow a single recessed unit to accommodate a range of bottle shapes/sizes, and/or to provide a degree of cushioning of the contents.

The gas filled envelope advantageously additionally provides a support module with a negligible radiation signature of its own. A particular problem in modifying moving conveyor systems for the conveyance of bottles and like containers, particularly those with a conventional circular cross-section and a tendency to roll, is the necessity of retaining the bottle in a stable and fixed relationship relative to the belt, so that its position is known as it passes through the scanning zone, so that its orientation is known, and so that the contents are not disturbed. This requires a support with a degree of functional rigidity. However, the provision of specific support structures with inherent structural rigidity, for example in the form of structures attached to the conveyor belt, or in the form of the rigid trays which are sometimes used in security scanning protocols, brings with it the complication that such materials might be thick enough themselves to have an attenuation effect on the scanning beam (e.g. by absorption and/or scattering). This is inherently disadvantageous, as it makes the accurate processing of the attenuation attributable to the bottle or like container and its contents harder to resolve effectively.

The solution conferred by the gas filled envelope embodiment provides a bottle support which has effective practical rigidity that is sufficient to meet the requirement to support bottles of a regular or irregular shape reliably, stably and consistently and to afford the opportunity for the operator to optimally position the bottle to present a best or representative profile as it is scanned through the system. However, because the material component is merely the thin film of the envelope, the support module has the immediate advantage of being effectively transparent across the scanning spectrum.

Support modules in accordance with the invention have further advantages, for example being easily fabricated, low cost and disposable, and can be easily marked with identifying markers, for example to indicate suitable container sizes, for positional sensing or calibration requirements. Established fabrication techniques are available. For example in the case of a support module comprising a gas filled envelope, webs of plastics film which are constructed to permit the production of patterns of air filled envelopes, cushions and pillows have been used extensively for cushioning objects to be transported in containers.

Moreover, unlike a conventional tray, a module in accordance with the invention could be fabricated in such a way as to allow an operator to position any bottle in a preferred orientation for scanning, for example to present a best or representative profile, to ensure that the bottle is scanned at a point where the contents are present etc.

It is particularly desirable that a conveyor system in accordance with the invention is configured to ensure that the position of any bottle or other container being scanned is stable and known as it passes through a scanning zone in the scanner, and in particular that the support module acts to prevent roll, yaw etc as the transverse conveyor moves to translate the bottle or like container to and through the scanning zone for scanning. In many instances it may for example be desirable for bottle orientation to be aligned in a known direction, which may be the direction of translation of the transverse conveyor.

To give effect to this, the module is preferably configured to define a recessed portion which tends to orient a container received thereon in a single preferred direction. A recess in general form of a groove or channel may be provided along a single direction and thereby tends to orientate a received container along such a preferred single direction. For example, in the preferred gas-filled envelope embodiment, the gas-filled envelope comprises a plurality of separately closed cellular volumes in a cellular arrangement which is symmetrical about and thereby tends to orientate a received container along such a preferred single direction. For example, the cellular arrangement comprises at least one cell each side of a mid-line which thereby defines a preferred orientation direction for a container received thereon. Conveniently therefore the cellular arrangement comprises one or more pairs of similar cells, with a cell of each such pair positioned either side of a mid-line which thereby defines a preferred orientation direction for a container received thereon. Conveniently therefore the cellular arrangement has mirror symmetry about such a mid-line.

When the gas-filled envelope is structured in this cellular way, an elongate container such as a bottle tends to be received with its long direction aligned with the mid-line axis of the structured cellular envelope and to be held in a stable and known position relative to, and for example aligned with, the direction of translation.

In a preferred embodiment, the gas-filled envelope comprises a cellular structure having an elongate direction, with at least one cell each side of a mid-line in the elongate direction, and which is mirror symmetrical about such a mid-line. Thus, in use, the long axis of the cellular envelope will tend to orient with the long direction and for example long axis of a bottle received stably upon it, and thereby allow the long direction of the bottle to be held in a stable and known position relative to, and for example aligned with, the direction of translation.

In order to align a received container such as a bottle in a fixed relationship with, and for example with its long direction and for example long axis aligned with, a translation direction of the transverse conveyor during use, a system in accordance with the invention preferably includes means to locate a support module in a fixed position and/or orientation relative to the conveyor surface. Such means may include suitable markings on a support module and/or on the conveyor surface to facilitate the relative positioning of support modules on the surface during use, and specific locator structures to locate a support module in a desired fixed position during use. Such support structures may provide for the detachable attachment and removal of support modules, but for many applications it may be most simple if support modules are located in suitable position in that a plurality of such support modules are fixed to the upper surface of the transverse conveyor.

The conveyor system includes a transverse conveyor having a conveyor surface to receive plural support modules, and in a possible embodiment having plural support modules fixedly mounted thereupon. The transverse conveyor is operable to translate the conveyor surface and support modules thereon (in use carrying containers of contained material) in a transverse translational direction to and through a scanning zone defined in a suitable scanner. Suitable drive means may be provided to effect this for example being adapted to cause movement of the conveyor surface in a transverse translational direction.

The transverse conveyor may comprise an endless conveyor element. The transverse conveyor may comprise a belt, chain or the like, an upper surface of which then constitutes the conveyor surface. The transverse conveyor is conveniently an endless belt conveyor.

A system in accordance with the invention preferably comprises a plurality of support modules. A suitable plurality of support modules may include plural alternative sizes and/or structures adapted for use with multiple bottle sizes, shapes etc to give the system versatility to deal with different bottles.

In use, a plurality of support modules may be distributed across the conveyor surface, for example in one or more rows arranged in a translation direction. In the case where support modules are fixedly attached to the conveyor surface, a plurality of support modules may be fixedly attached in distributed manner across the conveyor surface, for example in one or more rows arranged in a translation direction. Where plural rows are provided, the modules in any given row are preferably longitudinally offset in a transverse direction relative to other modules in any further rows, so that bottles pass successively but separately through the scanning zone.

A support module in accordance with the invention comprises in a preferred embodiment a gas-filled envelope configured to define a recessed portion for receiving a bottle or like container during use. As described above, the gas-filled envelope may for example be inflated to the degree necessary for such a recess to form inherently as a result of the weight of a container placed thereon, and/or may be specifically structured, for example by the provision of multiple cells, to effect this. A gas-filled envelope thus in effect forms an optionally cellular cushion which supports the bottle or like container.

The gas-filled envelope is partially inflated with air or another suitable light gas.

The web material of the envelope preferably comprises a thin film, typically for example no more than 50 μm thick. The combination of thin film and light gas has the advantage of being effectively transparent across the typical spectrum of the source used in the radiation detector through which the bottles are conveyed.

The web material of the envelope is preferably selected to be readily formable into the gas-filled cushion structures of the invention and to have a low attenuation profile across the typical spectrum of the source used in the radiation detector in any event. The web material of the envelope may for example be a suitable polymeric material, especially a thermoplastics material. Such plastics films have wide use in, for instance, packaging and related industries because of their low cost and the ease of forming them into a variety of shapes and wrapping capabilities and established techniques exist to fabricate cushion structures, and in particular cellular cushion structures, to serve as support modules in accordance with the invention. Thus, in the preferred case, the web material of the envelope is a thin film polymer sheet and especially a thermoplastics sheet. The film may be made from any suitable polymer or copolymer, for instance one selected from one or more of a polyolefin, a polyester, PET, PBT and an acrylic polymer. For instance, the film may be made from polypropylene The gas may additionally be selected to have a low attenuation profile across the typical spectrum of the source used in the radiation detector in any event. Suitable light gases with low x-ray attenuation include dry air and other mixtures of gases with low atomic number such as $N_2$, He, Ne.

An envelope making up a support module in accordance with the invention may conveniently be fabricated from two or more pieces of thin film sheet material of generally similar size laminated with their common perimeters sealed together in gas tight manner and/or with one or more thin film bag structures with their openings sealed in gas tight manner, in each case where the envelope or cellular volumes so defined have first been inflated to the required extent by filling with a suitable gas. If a cellular structure is required, such a cellular structure may suitably be fabricated either from multiple such structures, or by providing a single such structure with partial or complete additional closures internally of the perimeter. Such cellular gas filled structures and methods for their fabrication are known in, for instance, packaging and related industries, and similar structures are likely to be suitable to serve as gas-filled envelope support modules in accordance with the principles of the invention.

Seals between web surfaces to define an envelope/cellular structure in the manner above described may be effected by bonding the facing surfaces together for example adhesively, thermally, mechanically or otherwise. In the preferred case, a support module comprises an envelope formed of thin film polymer sheet and in particular thermoplastics sheet and, the sheet is thermally bonded to form a desired cushion and/or cellular cushion structure.

In a second more complete aspect of the invention, a scanning system is provided comprising a conveyor system in accordance with the first aspect of the invention in combination with a suitable object scanner.

The conveyor system is positioned to convey objects under test, comprising bottles or like containers of liquids or other materials having the same general homogenous characteristics, which are placed upon a conveyor surface, supported by suitable support modules as above described, and translated to and through the object scanner.

The object scanner is in a typical case a radiological scanner typically operating at a plurality of energies and/or over an energy range, for example comprising a radiation source and a radiation detector system spaced therefrom to define a scanning zone therebetween, the conveyor system being positioned to convey objects under test, comprising bottles or like containers of liquids or other materials having the same general homogenous characteristics, to and through the scanning zone.

The detector system is thus disposed to collect radiation after interaction with and for example in the preferred case after transmission through an object in the scanning zone in particular in an energy selective manner at a plurality of energies and/or over an energy range.

The detector system is in particular adapted to collect radiological information indicative of the material composition of an object in the scanning zone and the scanning system is therefore an apparatus is provided for the collection of compositional information from and for example identification of contained materials such as liquids and the like within containers.

Preferably the detector system is multispectral, in that the detector system is adapted to resolve radiation incident upon it spectroscopically into a plurality of energy bands and preferably at least three energy bands.

The detector system is thus compatible with existing numerical analysis techniques to determine compositional information from spectroscopically resolved transmitted radiation and/or from spectroscopically resolved attenuation data such as has been developed for static scanners such as described in International Patent Publication No. WO2009/024818 incorporated herein by reference.

However, throughput rates may be increased. Multiple items may be scanned, if not simultaneously a least immediately successively, as they are caused to pass through the scanning zone on a movable conveyor. The scanning system more closely parallels existing scanning protocols for security purposes than does a static prior art system.

The radiation source is preferably adapted to generate a two dimensional beam such as a fan beam or a curtain beam to obtain a slice transversely through an object as it passes through the scanner.

The detector system is preferably arranged and configured to receive incident radiation from such a two dimensional beam after transmission through the object and is preferably a linear array detector or a series of such linear array detectors.

The detector system is in particular preferably adapted to generate a transverse slice dataset from radiation transmitted as a transverse slice through an object as it passes through the scanner and includes transverse slice dataset generation module for this purpose. Optionally additionally the detector system may include a transverse slice dataset processing module to further process the data from the transverse slice dataset numerically to derive information pertinent to the composition of the contained material and/or to present the information as a viewable image. Optionally, the detector system further includes an image generation apparatus to generate at least a first image from the output of the detector system; and optionally further an image display adapted to display an image.

The radiation source is for example a source of high-energy radiation such as ionizing radiation, for example high energy electromagnetic radiation such as x-rays and/or gamma rays, or subatomic particle radiation, and the detector is adapted correspondingly to detect radiation in this spectrum. The radiation source for example is a broadband source such as a broadband x-ray or gamma-ray source capable of producing broad spectrum emission over a wide range of energies.

The detector system preferably exhibits a spectroscopically variable response across at least a part of the source spectrum allowing spectroscopic information to be retrieved and allowing intensity information to be detected at a plurality of differentiated energy bands and preferably at at least three differentiated energy bands across the spectrum of the source. In such a case the detector system preferably includes a data collection module to collect a dataset of intensity information about radiation incident at the detector resoled across said plurality of differentiated energy bands and a dataset processing module to further process the data from the dataset of intensity information numerically to derive information pertinent to the composition of the contained material and/or to present the information as a viewable image.

The detector system is preferably adapted to detect incident radiation in spectroscopically resolved manner in plural separate energy bands in the sense that it is adapted to differentiate incident radiation simultaneously into plural separate energy bands and preferably at least three such energy bands across the expected detection spectrum. For example, the detector system exhibits a spectroscopically variable response across at least a part of the expected detection spectrum allowing such simultaneous differentiation of incident radiation into a plurality of differentiated energy bands. Preferably incident radiation data is resolved spectroscopically between at least three energy bands simultaneously.

A suitable detector for implementation of the invention comprises one or more detector elements of a semiconductor material adapted for high energy physics applications, such as a material able to act as a detector for high energy radiation, and for example high energy electromagnetic radiation such as x-rays or gamma rays, or subatomic particle radiation. The resultant detector element comprises at least one layer of such material and is thus a device adapted for high energy physics applications, and for example a detector for high energy radiation such as x-rays or gamma rays, or subatomic particle radiation.

In accordance with the preferred embodiment, collected data is resolved spectroscopically across at least two and preferably at least three and for example many energy bands within the spectrum of the source. The semiconductor material of at least one of the detector elements is preferably a material adapted to exhibit a spectroscopically variable response across at least a substantial part of the intended radiation spectrum in use. In particular a semiconductor material is used that exhibits inherently as a direct material property a direct variable electrical and for example photoelectric response to different parts of the radiation spectrum in use.

In a preferred embodiment the semiconductor material is formed as a bulk crystal, and for example as a bulk single crystal (where bulk crystal in this context indicates a thickness of at least 500 µm, and preferably of at least 1 mm).

In a preferred embodiment the semiconductor material may be selected from Group II-VI semiconductors and in particular may be selected from cadmium telluride, cadmium zinc telluride (CZT), cadmium manganese telluride (CMT), and alloys thereof, and for example, save for incidental impurities, consists essentially of crystalline $Cd_{1-(a+b)}Mn_aZn_b Te$ where $a+b<1$ and a and/or b may be zero. A detector may also have other detector elements of other materials for additional functionality.

In a further aspect of the invention, there is provided a method of conveying contained materials such as liquids and the like, especially within containers such as bottles, to and through such a scanner.

The method comprises:

providing a transverse conveyor having a conveyor surface;

providing a plurality of container support modules each adapted to seat on the conveyor surface, wherein each container support module comprises a lower surface that sits upon the conveyor surface of the conveyor and an upper part in which a container-receiving recessed portion is defined and for example comprises a gas-filled envelope as above described so configured as to define a container receiving recessed portion;

disposing at least one container support module on the conveyor surface;

placing at least one container on a container support module;

translating the transverse conveyor to cause the at least one container and container support module to move to and through a scanner.

The method is thus a method of use of the conveyor system of the first aspect of the invention or the scanning system of the second aspect of the invention and preferred features will be understood by analogy.

In the preferred case in particular the step of causing the at least one container and container support module to move to and through a scanner comprises specifically:

providing a radiation source and a radiation detector system spaced therefrom to define a scanning zone therebetween;

translating the transverse conveyor to cause the at least one container and container support module to move through the scanning zone;

collecting radiation incident at the detector after interaction with and for example transmission through the at least one container in the scanning zone.

In the preferred case in particular the method is deployed as a method of collection of radiological information indicative of the material composition of the contents of the at least one container in the scanning zone and the scanner is preferably an apparatus adapted for the collection of compositional information from and for example identification of contained materials such as liquids and the like within containers and the method includes the further step of deriving information indicative of the material composition of the contents of the at least one container from the collected radiation incident at the detector after interaction with and for example transmission through the at least one container in the scanning zone.

In the preferred case in particular the method makes use of spectroscopically resolved radiation incident at the detector to derive information indicative of the material composition of the contents of the at least one container, and includes the step of resolving the radiation spectroscopically into a plurality of energy bands and preferably at least three energy bands spaced across a spectrum of the source radiation.

The invention will now be described by way of example only with reference to FIGS. 1 to 3 of the accompanying drawings in which.

Figure 1:
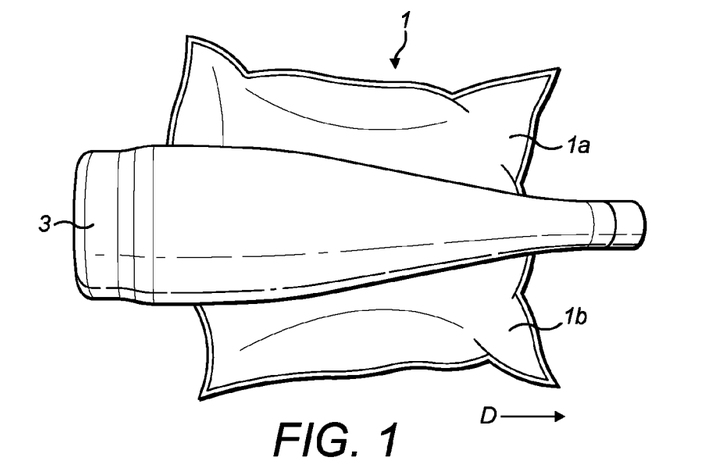
FIG. 1 is an illustration of a single bottle in position on a support module embodying the principles of the invention.

FIG. 1 shows a view from above of a simple cellular cushion comprising an embodiment of modular support structure in accordance with the principles of the invention. The cellular cushion 1 comprises a single cell either side of a mid-line (cells 1a, 1b) which defines a bottle alignment direction D parallel to an elongate axis of the cellular cushion 1. The cellular cushion is effectively mirror symmetrical about this axis.

The cellular cushion 1 is made from a thin plastics film partly inflated with air or other light gas. This provides a low cost disposable support system which can hold a bottle 3 suitably in position aligned with its long direction in the direction D, and retain it stably in use on a conveyor belt. The support only consists of thin light materials that do not significantly modify the intensity or the spectrum of a polychromatic x-ray beam with may be used to irradiate a bottle carried upon it.

This is importance potentially significant advantage in the intended principal application of the invention where the modification to such a transmitted x-ray spectrum by attenuation through bottle and contents is used as the basis for materials identification. Using such a support means that the interpretation of the material contents of a scanned bottle is not affected by the supporting structure.

A support structure with a very low x-ray attenuation provides for more widespread applicability for a range of applications, in particular for example where it is desirable to scan a range of containers with a range of potential responses, and the complication of removing attenuation attributable to the container makes the data harder to interpret.

A support structure based on the cellular cushion principle, rather than the more rigidly structured and defined container-receiving recessed portion that might be provided for example in a support structure fabricated from a foam or light polymeric material, is also more flexible in its ability to receive and to stably support a range of differently-sized and -shaped containers. Again therefore it provides for more widespread applicability where it is desirable to scan a range of containers.

The example support structure of the embodiment based on the cellular cushion principle is therefore optimized for universal application, for example in security applications where a range of shapes, sizes, contents etc need to be tested. However, in many scenarios, particularly where only a few shapes, sizes, contents etc are to be tested, for example for quality control or testing of known objects, other support solutions may be just as applicable, and the cellular cushion embodiment will be understood to be an example only.

Figure 2:
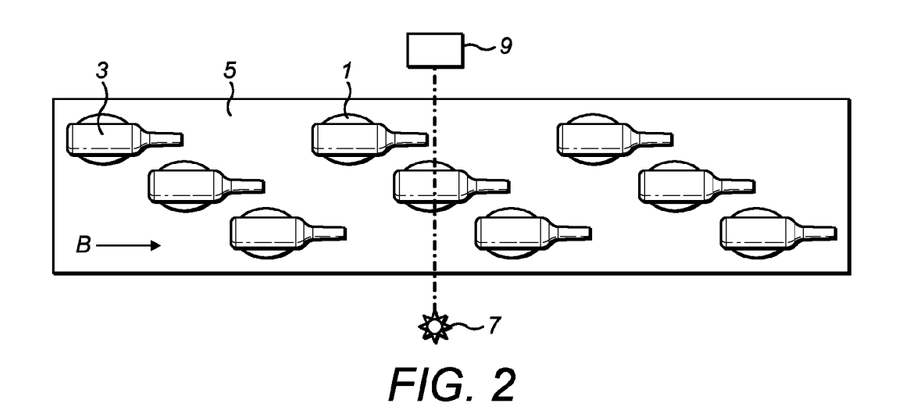
FIG. 2 is an illustration of a conveyor system comprising plural such support modules, shown in plan view in use in conjunction with a radiation source and detector.

The supporting structure is compliant with use in a belt fed scanner system as illustrated in FIG. 2. Multiple such supporting structures in place on a conveyor belt 5 are illustrated from above.

Multiple cellular cushions 1, supporting multiple bottles 3, are provided arrayed on an upper surface 5 of a conveyor belt which transports the supported bottles in a belt direction B. The cellular cushions allow for the orientation of the bottle, which it is usually desirable to align to the direction of belt travel, to be simply achieved by an operator. In the illustrated embodiment, the direction of travel of the belt B is the same as the orientation direction of the bottle D.

The conveyor belt 5 moves the bottle and support arrangements in a traversing direction B towards and through a scanner. The scanner in the embodiment is one that utilises scan beams that are orthogonal, nominally recording x-ray projection data of slices through the target medium and at a number of x-ray energies, facilitated by energy selective detection technology.

The slice is conveniently a one or two dimensional transmission radiograph. The collected data may be numerically analysed. For example the scanner is adapted to use transmission intensity data to generate a one- or two-dimensional image of an object in an x, y plane generally perpendicular to an incident radiation transmission path and/or to process such transmission intensity data from a slice of an object in an x, y plane for example to obtain information about the material composition of container and/or contents.

The scanner provides a scanning zone defined by a polychromatic x-ray source 7 and a multispectral x-ray detector 9. Such a source and detector arrangement is used to obtain spectroscopically resolved attenuation information, resolved across at least two and preferably at least three energy bands of the polychromatic x-ray source as the polychromatic x-ray beam traverses bottle and contents, and this attenuation information may then be used as the basis for materials analysis/identification, for example by numerical processing embodying the principles of International Patent Publication No. WO2009/024818.

In the illustrated example, it can be seen that the cellular support structure is incorporated in a fixed pattern onto a belt of a scanner system, so that the bottles lie in three rows in a staggered array so that they can be closely successively but separately scanned as the belt moves in the direction B. This allows high throughput rates while avoiding the problem which might arise in the event of the simultaneous scanning of multiple bottles, and the difficulty in deciphering information from such multiple bottle scans, as the traversal by the x-ray beam of single bottle slices can be separately identified.

In the illustrated embodiment, the multiple cellular cushions 1 are fixed on the surface of the scanner, to ensure consistent orientation of the bottles in a direction D parallel to a belt direction B, but arrangements in which the cushions are detachable or otherwise aligned could be envisaged. The lower surface may be provided with a high friction material for example. Bottle orientation may thus be aligned to the direction of translation allowing for the possibility for the lateral position of the bottle being in a stable and known position.

Optionally, and not shown in the example, the upper part of the film may be modified to provide a collar portion adapted in use to encircle the neck of a bottle to retain the bottle more stably and rigidly in a fixed position and orientation.

The thin film membrane of the support cushion may be labelled, for example using suitable print technology, with identifying, calibration and positional markers as required.

Figure 3:
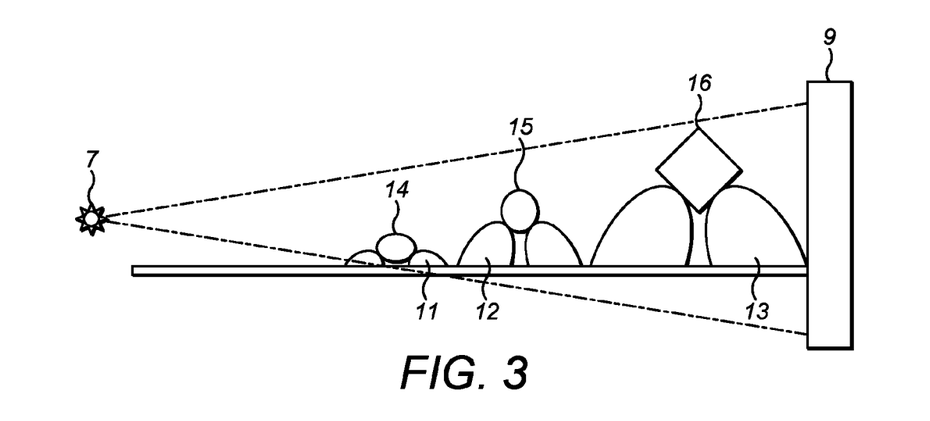
FIG. 3 is a schematic illustration in cross-section through the scanning zone to show the option of using multiple sizes of support module.

FIG. 3 is a representation in schematic cross-section through the scanning zone defined between a source 7 and detector 9, and illustrates the option to provide plural differently sized supports (11, 12, 13) for differently sized/shaped bottles (14, 15, 16) and/or to retain bottles in different positions in the scanning zone.

Thus, the system provides a versatile solution that has a minimal effect on the attenuation of the x-ray beam, allowing insertion of multiple bottle shapes and sizes, supporting bottles of a regular shape reliably, stably and consistently, and affording the opportunity for the operator to position the bottle as required and provide effective scanning.

The invention claimed is:

1. A conveyor system for use with a scanning apparatus for scanning of contained materials within containers, comprising:
 a transverse conveyor having a conveyor surface;
 a plurality of container support modules each adapted to seat on the conveyor surface;
 wherein each container support module comprises a lower surface that sits upon the conveyor surface of the conveyor and upper part in which a container-receiving recessed portion is defined; and
 wherein the container support module is a gas-filled envelope comprising a plurality of separately closed cellular volumes in a cellular arrangement that is symmetrical about an axis of the container support module and tends to orient a received container along a preferred single direction.

2. The conveyor system in accordance with claim 1, wherein at least the portion of the container support module comprising the recess in the upper surface is resiliently deformable.

3. The conveyor system in accordance with claim 1, wherein the recess in the upper surface is configured in use to be resiliently deformable as a bottle is placed therein, into a deformed configuration where the bottle is held stably and rigidly contained in a fixed position and orientation.

4. The conveyor system in accordance with claim 1, wherein the gas-filled envelope defines a container-receiving recessed portion.

5. The conveyor system in accordance with claim 4, wherein the gas-filled envelope comprises at least one closed cellular volume defined by a gas-impermeable web material inflated to a desired extent with a gas.

6. The conveyor system in accordance with claim 5, wherein the gas-filled envelope comprises a plurality of separately closed cellular volumes.

7. The conveyor system in accordance with claim 5, wherein the gas-impermeable web material comprises a flexible thin film material.

8. A conveyor system in accordance with claim 5, wherein the gas-impermeable web material comprises a polymer sheet.

9. The conveyor system in accordance with claim 8, wherein the gas-impermeable web material comprises a thermoplastics sheet.

10. The conveyor system in accordance with claim 8, wherein the polymer sheet is thermally bonded to form at least one of a cushion and cellular cushion structure.

11. The conveyor system in accordance with claim 4, wherein the gas-filled envelope comprises a gas-impermeable web having a lower surface that sits upon the conveyor surface of the conveyor so as to present an upper part in which a container receiving recessed portion is defined.

12. The conveyor system in accordance with claim 1, wherein the container support module is configured to define a recessed portion which tends to orient a container received thereon in a single preferred direction.

13. The conveyor system in accordance with claim 1, wherein the gas-filled envelope comprises a plurality of separately closed cellular volumes in a cellular arrangement comprising at least one cell each side of a mid-line.

14. The conveyor system in accordance with claim 13, wherein the cellular arrangement comprises one or more pairs of similar cells, with a cell of each such similar pair positioned either side of a mid-line.

15. The conveyor system in accordance with claim 1, further comprising means to locate a support module in at least one of a fixed position and an orientation relative to the conveyor surface.

16. The conveyor system in accordance with claim 15, comprising locator structures to locate a support module in a desired fixed position and/or orientation relative to the conveyor surface during use.

17. The conveyor system in accordance with claim 1, wherein a plurality of support modules are fixed to the conveyor surface of the transverse conveyor.

18. The conveyor system in accordance with claim 17, wherein a plurality of support modules are distributed across the conveyor surface in one or more rows arranged in a translation direction.

19. The conveyor system in accordance with claim 1, wherein the transverse conveyor is an endless belt conveyor.

20. The conveyor system in accordance with claim 1, comprising a plurality of support modules including at least one of plural alternative sizes and structures.

21. A scanning system comprising a conveyor system in accordance with claim 1 additionally provided with an object scanner.

22. The scanning system in accordance with claim 21, wherein the object scanner is a radiological scanner.

23. The scanning system in accordance with claim 22, wherein the radiological scanner comprises a radiation source and a radiation detector system spaced therefrom to define a scanning zone therebetween, the conveyor system being positioned to convey objects to and through the scanning zone.

24. The conveyor system in accordance with claim 23 comprising a plurality of rows, wherein the plurality of container support modules in any given row are longitudinally offset in a translation direction relative to other modules in any further rows, so that bottles pass successively but separately through the scanning zone.

25. The scanning system in accordance with claim 23, wherein the radiation detector system is disposed to collect radiation after transmission through an object in the scanning zone.

26. The scanning system in accordance with claim 23, wherein the radiation detector system is adapted to resolve radiation incident upon it spectroscopically into a plurality of energy bands.

27. The scanning system in accordance with claim 26, wherein the radiation detector system is adapted to resolve radiation incident upon the detector spectroscopically into at least three energy bands.

28. The scanning system in accordance with claim 23, wherein the radiation source is adapted to generate a two dimensional beam through an object as it passes through the radiological scanner.

29. The scanning system in accordance with claim 28, wherein the radiation detector system is arranged and configured to receive incident radiation from such a two dimensional beam after transmission through the object and is preferably a linear array detector or a series of such linear array detectors.

30. The scanning system in accordance with claim 23, wherein the radiation detector system is adapted to generate a transverse slice dataset from radiation transmitted as a transverse slice through an object as it passes through the scanner and includes transverse slice dataset generation module for this purpose.

31. The scanning system in accordance with claim 23, wherein the radiation source is high energy electromagnetic radiation comprising at least one of x-rays, gamma rays, and subatomic particle radiation.

32. The scanning system in accordance with claim 23, wherein the radiation detector system is adapted to detect incident radiation in spectroscopically resolved manner in plural separate energy bands in the sense that it is adapted to differentiate incident radiation simultaneously into plural separate energy bands across a spectrum of the radiation source.

33. The scanning system in accordance claim 23, wherein the radiation detector system comprises a material adapted to exhibit a spectroscopically variable response across at least a substantial part of an intended radiation spectrum in use.

34. The scanning system in accordance with claim 33, wherein the radiation detector system comprises a material adapted to exhibit inherently as a direct material property a direct variable photoelectric response to different parts of the radiation spectrum in use.

35. The scanning system in accordance with claim 34, wherein the detector material is selected from cadmium telluride, cadmium zinc telluride (CZT), cadmium manganese telluride (CMT), and alloys thereof.

36. An apparatus in accordance with claim 35 wherein the detector material, save for incidental impurities, consists essentially of crystalline $Cd_{1-(a+b)}Mn_aZn_bTe$ where $a+b<1$ and a and/or b may be zero.

37. A method of conveying contained materials in containers through a scanner comprising the steps of:
providing a transverse conveyor having a conveyor surface;
providing a plurality of container support modules each adapted to seat on the transverse conveyor surface, wherein each container support module comprises a lower surface that sits upon the conveyor surface of the conveyor and upper part in which a container-receiving recessed portion is defined;
disposing at least one container support module on the conveyor surface;
placing at least one container on a container support module;
translating the transverse conveyor to cause the at least one container and container support module to move to and through a scanner; and
wherein the container support module is a gas-filled envelope comprising a plurality of separately closed cellular volumes in a cellular arrangement that is symmetrical about an axis of the container support module and tends to orient a received container along a preferred single direction.

38. The method of claim 37, wherein the container support module comprises a gas-filled envelope so configured as to define the container-receiving recessed portion.

39. The method of claim 37, wherein the step of causing the at least one container and container support module to move to and through a scanner comprises specifically:
providing a radiation source and a radiation detector system spaced therefrom to define a scanning zone therebetween;
translating the transverse conveyor to cause the at least one container and container support module to move through the scanning zone;
collecting radiation incident at the radiation detector after interaction with and for example transmission through the at least one container in the scanning zone.

40. The method of claim 39 further comprising deriving information indicative of material composition of the contents of the at least one container from the collected radiation incident at the radiation detector after interaction with and for example transmission through the at least one container in the scanning zone.

41. The method of claim 40 further comprising resolving the radiation incident at the detector spectroscopically into a plurality of energy bands and preferably at least three energy bands spaced across a spectrum of the source radiation and using the spectroscopically resolved radiation to derive information indicative of the material composition of the contents of the at least one container.

* * * * *